US008852183B2

(12) United States Patent
Boulnois et al.

(10) Patent No.: US 8,852,183 B2
(45) Date of Patent: Oct. 7, 2014

(54) SCISSOR TIP FOR BIPOLAR HIGH FREQUENCY ENDOSCOPE

(75) Inventors: Jean-Luc Boulnois, Boston, MA (US); David Strome, Newtown, PA (US); Charles Faust, Bensalem, PA (US); James Barnitz, Skippack, PA (US); Peter Aliski, Malden, MA (US)

(73) Assignee: Microline Surgical Inc., Beverly, MA (US)

( * ) Notice: Subject to any disclaimer, the term of this patent is extended or adjusted under 35 U.S.C. 154(b) by 207 days.

(21) Appl. No.: 12/691,942

(22) Filed: Jan. 22, 2010

(65) Prior Publication Data
US 2010/0312240 A1 Dec. 9, 2010

Related U.S. Application Data

(63) Continuation of application No. 12/478,945, filed on Jun. 5, 2009, now abandoned.

(51) Int. Cl.
*A61B 18/12* (2006.01)
*A61B 18/14* (2006.01)
*A61B 17/32* (2006.01)
A61B 17/00 (2006.01)
A61B 17/3201 (2006.01)
A61B 17/28 (2006.01)
A61B 17/29 (2006.01)

(52) U.S. Cl.
CPC ..... *A61B 18/1445* (2013.01); *A61B 2017/0088* (2013.01); *A61B 17/3201* (2013.01); *A61B 2018/1455* (2013.01); *A61B 2017/2825* (2013.01); *A61B 2018/126* (2013.01); *A61B 2017/2945* (2013.01); *A61B 17/320016* (2013.01); *A61B 2018/1432* (2013.01)

USPC ................................................ 606/48
(58) Field of Classification Search
USPC .................... 606/41, 45, 48, 51, 52
See application file for complete search history.

(56) References Cited

U.S. PATENT DOCUMENTS

| 4,041,952 | A | * | 8/1977 | Morrison et al. ............... 606/42 |
| 5,041,519 | A | | 8/1991 | Pan et al. |
| 5,171,258 | A | | 12/1992 | Bales et al. |
| 5,325,289 | A | | 6/1994 | Togawa |
| 5,330,471 | A | | 7/1994 | Eggers |
| 5,352,222 | A | | 10/1994 | Rydell |

(Continued)

FOREIGN PATENT DOCUMENTS

DE 19855812 6/2000
EP 0850598 7/1998

(Continued)

OTHER PUBLICATIONS

E.P.O. Office action, mail date is Jun. 23, 2011.

(Continued)

*Primary Examiner* — Michael Peffley
*Assistant Examiner* — Daniel Fowler
(74) *Attorney, Agent, or Firm* — Greenblum & Bernstein, P.L.C.

(57) ABSTRACT

A bipolar scissor for cutting and coagulating tissue includes a first blade having a first cutting edge and a first shearing blade surface and a second blade having a second cutting edge and a second shearing blade surface. Additionally, one of the first and second blades may include a non-conductive material having an embedded electrode.

26 Claims, 14 Drawing Sheets

(56) References Cited

U.S. PATENT DOCUMENTS

| | | | |
|---|---|---|---|
| 5,352,223 A * | 10/1994 | McBrayer et al. ............ 606/51 |
| 5,356,408 A | 10/1994 | Rydell |
| 5,391,166 A | 2/1995 | Eggers |
| 5,396,900 A | 3/1995 | Slater et al. |
| 5,462,546 A | 10/1995 | Rydell |
| 5,478,347 A * | 12/1995 | Aranyi ...................... 606/170 |
| 5,514,134 A | 5/1996 | Rydell et al. |
| 5,540,685 A | 7/1996 | Parins et al. |
| 5,569,243 A | 10/1996 | Kortenbach et al. |
| 5,700,261 A | 12/1997 | Brinkerhoff |
| 5,776,128 A | 7/1998 | Eggers |
| 5,779,701 A | 7/1998 | McBrayer et al. |
| 5,810,808 A | 9/1998 | Eggers |
| 5,827,281 A | 10/1998 | Levin |
| 5,891,140 A | 4/1999 | Ginn et al. |
| 5,908,420 A | 6/1999 | Parins et al. |
| 5,951,549 A | 9/1999 | Richardson et al. |
| 5,954,720 A | 9/1999 | Wilson et al. |
| 5,976,130 A | 11/1999 | McBrayer et al. |
| 5,976,132 A | 11/1999 | Morris |
| 5,997,533 A * | 12/1999 | Kuhns ........................ 606/41 |
| 6,001,096 A | 12/1999 | Bissinger et al. |
| RE36,795 E | 7/2000 | Rydell |
| 6,090,108 A | 7/2000 | McBrayer et al. |
| 6,113,596 A | 9/2000 | Hooven et al. |
| 6,312,430 B1 | 11/2001 | Wilson et al. |
| 6,350,264 B1 | 2/2002 | Hooven |
| 6,391,029 B1 | 5/2002 | Hooven et al. |
| 6,447,511 B1 | 9/2002 | Slater |
| 6,464,701 B1 | 10/2002 | Hooven et al. |
| 6,589,235 B2 * | 7/2003 | Wong et al. .................. 606/32 |
| 2002/0019632 A1 | 2/2002 | Mayenberger |
| 2004/0186348 A1 | 9/2004 | Kidooka |
| 2004/0199160 A1 * | 10/2004 | Slater ............................ 606/48 |
| 2005/0096650 A1 | 5/2005 | Ouchi |
| 2005/0137453 A1 | 6/2005 | Ouchi et al. |
| 2009/0198228 A1 | 8/2009 | Sartor |

FOREIGN PATENT DOCUMENTS

| | | |
|---|---|---|
| EP | 2085046 | 8/2009 |
| JP | 10-192295 | 7/1998 |
| JP | 2006-198233 | 8/2006 |
| WO | 96/27338 | 9/1996 |
| WO | 96/33665 | 10/1996 |

OTHER PUBLICATIONS

Canada Office action, mail date is Mar. 28, 2012.
Japan Office action, mail date is Apr. 3, 2012.
E.P.O. Office action, mail date is Sep. 11, 2013.

* cited by examiner

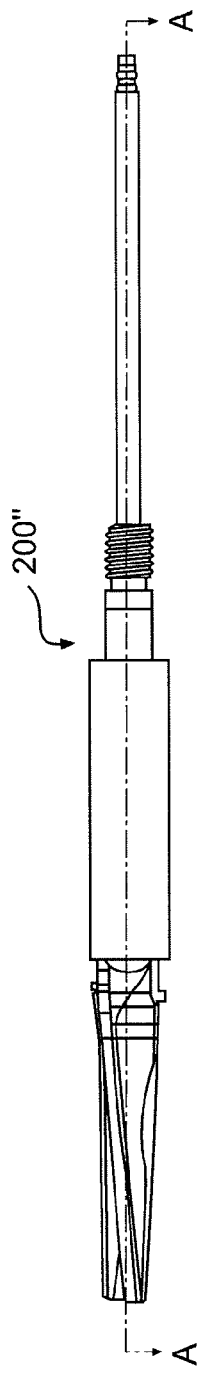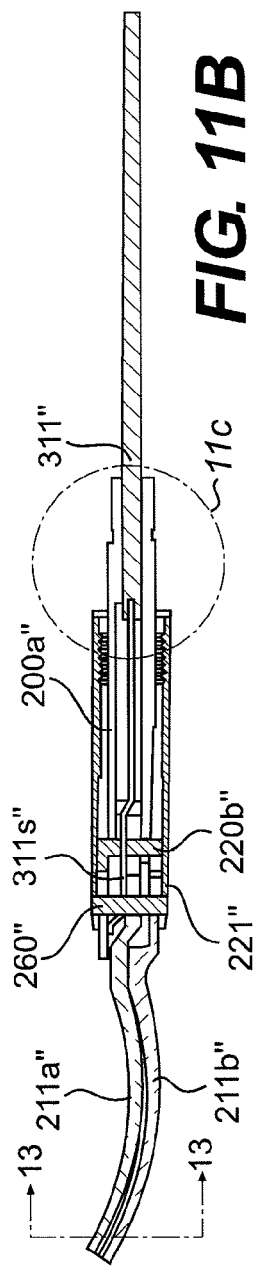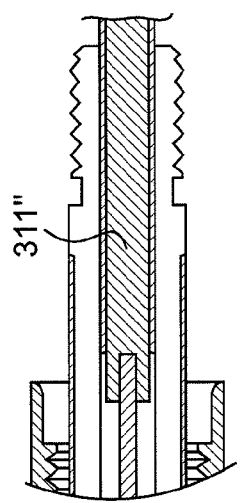

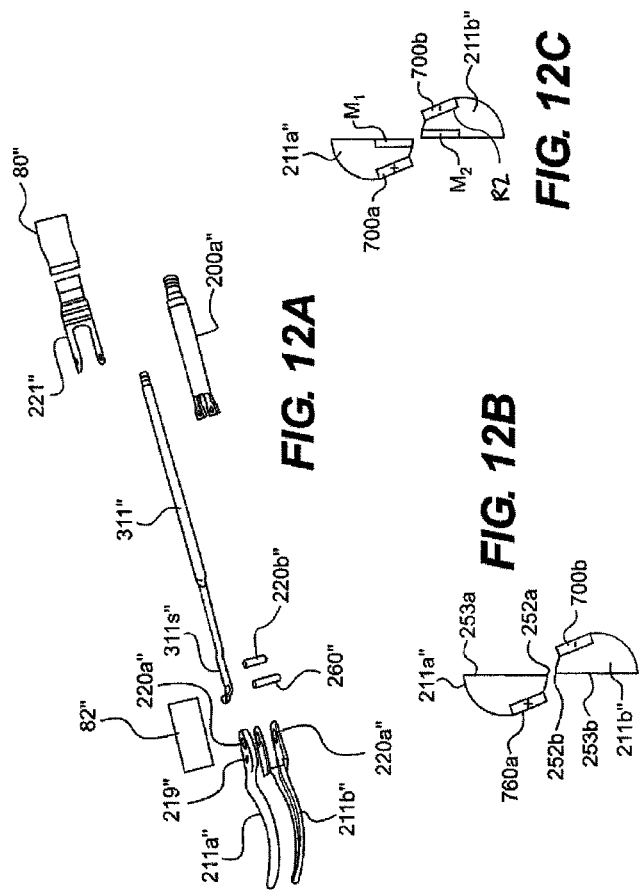

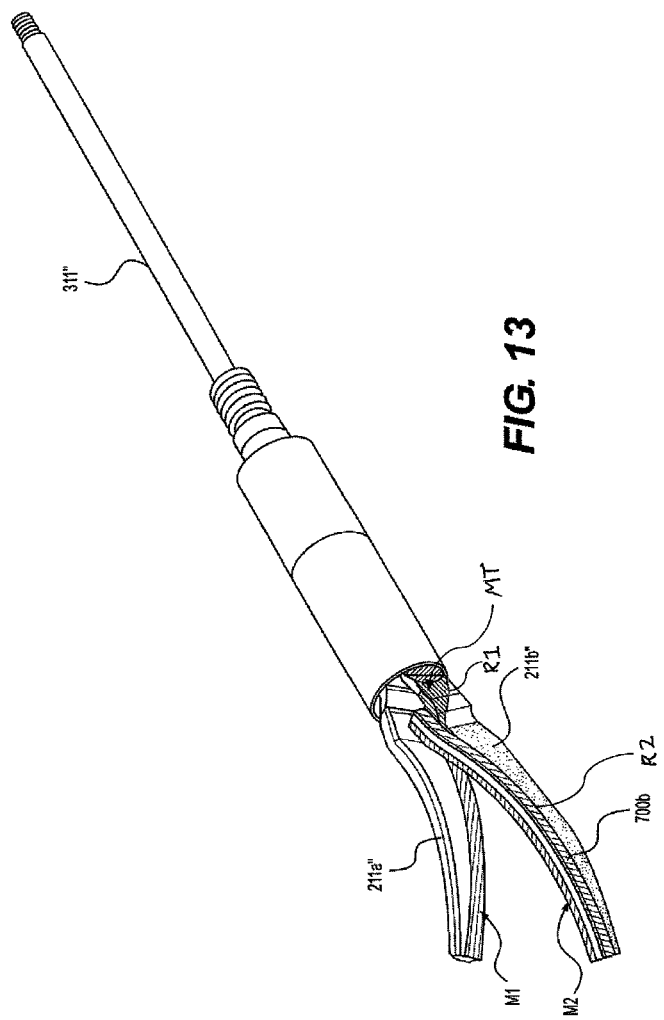

SCISSOR TIP FOR BIPOLAR HIGH FREQUENCY ENDOSCOPE

CROSS-REFERENCE TO RELATED APPLICATION

The present application is a continuation of pending U.S. patent application Ser. No. 12/478,945, filed on Jun. 5, 2009, the disclosure of this application are expressly incorporated by reference herein in its entirety.

BACKGROUND OF THE INVENTION

I. Field of the Invention

This invention relates generally to electrosurgical instruments, and more particularly to a bipolar scissor having an embedded electrode. The bipolar scissor may be used in a laparoscopic procedure, or any other desirable endoscopic procedure.

II. Discussion of the Prior Art

In the conventional art, heat has been used for the cauterization of bleeding wounds in various surgical procedures. For example, the use of radio frequency (RF) energy traveling through the body has been widely used to stop bleeding. In this regard, at least two modes of cauterization are typically employed, namely monopolar or bipolar coagulation.

The prior art monopolar surgical instruments usually include a generator, an active electrode of small dimensions, and a large area return or dispersive electrode designed to be placed on the patient's body to serve as a return point for the energy released at the active electrode site. In this regard, the active electrode is applied to the bleeding site and the current path is completed through the body to the return electrode which is electrically in contact with the patient's body.

Bipolar surgical instruments have an inherent advantage over monopolar surgical instrument of containing energy generated at the surgical instrument. In a bipolar surgical instrument, both the active and the return electrodes are placed on the surgical instrument. Thus, no separate return electrode on the patient is required as in monopolar systems. Therefore, the generated energy remains at the site where the surgical instrument is being used and only affects patient tissue in close proximity.

Some bipolar scissors allow simultaneous cautery and cutting of tissue. Typically the base construction of the blades is metal with a layer of insulating material located on one of the shearing surfaces and the hinge pin to provide electrical isolation between the bipolar electrodes. A later advancement on this basic approach was to provide a layer of insulation between the base metal blade and a thin metal shearing surface to provide electrical isolation between the bipolar electrodes and allow for a more durable shearing surface.

The conventional art also discloses a base construction of ceramic material instead of metal with a metal coating applied to the outside edge of the ceramic body to act as the electrosurgical electrode. Additionally, the conventional art also discloses a laminated design that uses a base construction of ceramic material with metal applied to both the outside edge of the ceramic body to act at the electrosurgical electrode and the inside edge of the ceramic body to serve as the shearing surface. However, the conventional art laminated design may be structurally compromised when laminating materials having different material properties. For example, material characteristics such as thermal expansion and contraction properties may result in a laminated scissor (or blade) being weakened due to stresses caused by expansion and contraction of the composite materials.

SUMMARY OF THE INVENTION

Accordingly, a non-limiting embodiment of the present invention provides a bipolar scissor for cutting and coagulating tissue. The bipolar scissor may include a first blade having a first cutting edge and a first shearing blade surface, and a second blade having a second cutting edge and a second shearing blade surface. The first and second blades may include a non-conductive material having an embedded electrode.

Further, in accordance with an additional feature, the non-conductive material may be provided with an insert recess which receives the embedded electrode and a metallization recess provided with a metallization. In this regard, the metallization may extend into the insert recess and electrically contact the embedded electrode. Additionally, the insert recess and the metallization recess may be formed integral with each other. Also, the embedded electrode may be brazed onto the non-conductive material.

In an additional non-limiting feature each of the first and second blades may include a non-conductive material. In this regard, the first blade may have a first embedded electrode and the second blade may have a second embedded electrode, the first and second electrodes being polar opposites of each other.

In yet another non-limiting feature, the first electrode may be embedded at an outer surface of the first blade and the second electrode may be embedded at an outer surface of the second blade. Further, the one of the first and second blades having the embedded electrode may include a metal shearing surface embedded in the non-conductive material at the shearing blade surface.

According to another embodiment, the non-conductive material, of the at least one of the first and second blades, may include a ceramic material and the embedded electrode may include a metal insert. Further, the other of the at least one of the first and second blades may include metal.

According to another feature, both the first and second blades may be provided with metal shearing surfaces. For example, the first blade may include a first metal shearing surface embedded in the non-conductive material at the first shearing blade surface and the second blade may include a second metal shearing surface embedded in the non-conductive material at the second shearing blade surface. Also, the non-conductive material may electrically isolate the embedded electrode from the metal shearing blade surface. Further, the non-conductive material may include a ceramic material.

In a further embodiment, at least one of the first and second blades may include a non-conductive material having an electrode. In this regard, the electrode may be provided as a metal coating opposite the shearing blade surface of the at least one of the first and second blades which includes the non-conductive material. Additionally, the non-conductive material may include a ceramic material and the other of the at least one of the first and second blades may include metal.

Further, in another embodiment, both the first and second blades may include a non-conductive material. In this regard, each of the first and second blades may have a metal insert provided at corresponding cutting edges of the first and second blades. Further, the metal coating may be provided on both the first and second blades opposite corresponding shearing blade surfaces. Further, the non-conductive material may include a ceramic material.

In an additional feature, a surgical tool assembly, configured to be connected to a distal end of a bipolar surgical instrument having first and second electrical conductors, may also be provided. The surgical tool assembly may include a scissor including the first and second blades, as discussed above. In this regard, the one of the first and second blades having the embedded electrode may be configured to be electrically connected to one of the first and second electrical conductors of the bipolar surgical instrument.

Further, and in accordance with another feature, the surgical tool assembly may include an elongated connector configured to electrically connect the at least one embedded electrode of the one of the first and second blades to one of the first and second electrical conductors.

In this regard, the elongated connector may be configured to electrically connect the first embedded electrode to the first electrical conductor. Also, the surgical tool assembly may include and a blade support configured to electrically connect the second embedded electrode to the second electrical conductor.

In yet still another feature, the elongated connector may include a spring provided at a distal end of the elongated connector. In this regard, the spring may be configured to bias the first blade into contact with the second blade and electrically connect the first blade to one of the first and second electrical conductors. Further, the blade support may include a fork-shaped cylinder provided at a distal end of the surgical tool assembly. Additionally, the blade support may include a pivot pin, the first and second blades being configured to rotate about the pivot pin so as to open and close.

In another feature, a first cam may be provided at a proximal end of the first blade and a second cam may be provided at a proximal end of the second blade. Further, a cam follower may be coupled to the first and second cams and a distal end of a plunger may be configured to reciprocate axially. In this regard, axial movement of the plunger may actuate the cam follower such that the first and second blades open and close in accordance with a direction of axial movement of the plunger.

In an additional feature, a bipolar surgical instrument may include the surgical tool assembly, as discussed above. For example, the bipolar surgical instrument may include a connector coupled to and configured to actuate first and second blades.

In this regard, the bipolar surgical instrument may include an inner shaft assembly having an inner shaft; an intermediate shaft assembly having an intermediate shaft; and an outer shaft assembly having an outer shaft. For example, the intermediate and inner shaft assemblies may be generally positioned within the outer shaft assembly, and the inner shaft assembly may be generally positioned within the intermediate shaft assembly.

Further, a first connector may be coupled to the inner shaft assembly and a second connector may be coupled to and configured to move the intermediate shaft assembly.

Additionally, a main body housing may be coupled to the first and second connectors. Also, at least one electrical contact electrically may electrically contact a peripheral surface of at least one of the inner, intermediate and outer shafts. In this regard, the at least one electrical contact may be configured to allow uninterrupted and continuous rotation of the main body housing relative to the at least one of the inner, intermediate and outer shafts which the electrical contact contacts. Further, the at least one electrical contact may be a canted coil spring.

BRIEF DESCRIPTION OF THE DRAWINGS

The present invention is further described in the detail description which follows, in reference to the noted plurality of drawings, by way of non-limiting examples of preferred embodiments of the present invention, in which like characters represent like elements throughout the several views of the drawings, and wherein:

FIG. 11A is a top plan view of a scissor-type surgical tool assembly of a third non-limiting embodiment;

FIG. 11B is a cross-sectional view of the scissor-type surgical tool of the third non-limiting embodiment;

FIG. 11C is an exploded view of a threaded connection of the non-limiting third embodiment;

FIG. 12A is an exploded view of a surgical tool assembly according to the third non-limiting embodiment of the present invention;

FIG. 12B is a cross-sectional view of the scissor having, e.g., a ceramic shearing surface;

FIG. 12C is a cross-sectional view of the scissor having, e.g., a metal shearing surface;

FIG. 13 is a perspective view of the scissor-type surgical tool of the third non-limiting embodiment.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
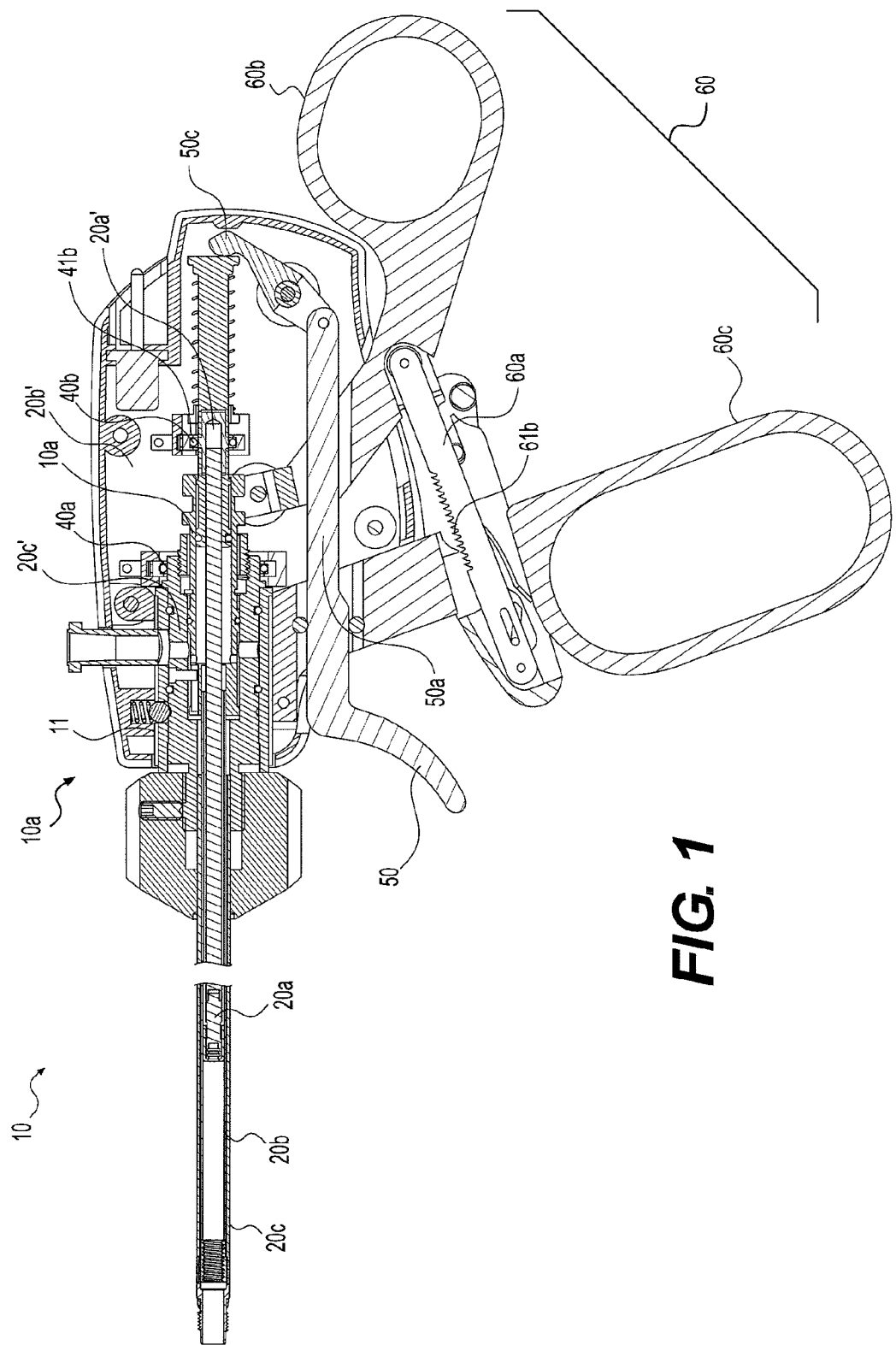
FIG. 1 is a cross-sectional view of a bipolar surgical instrument according to a non-limiting embodiment of the present invention.
Figure 2:
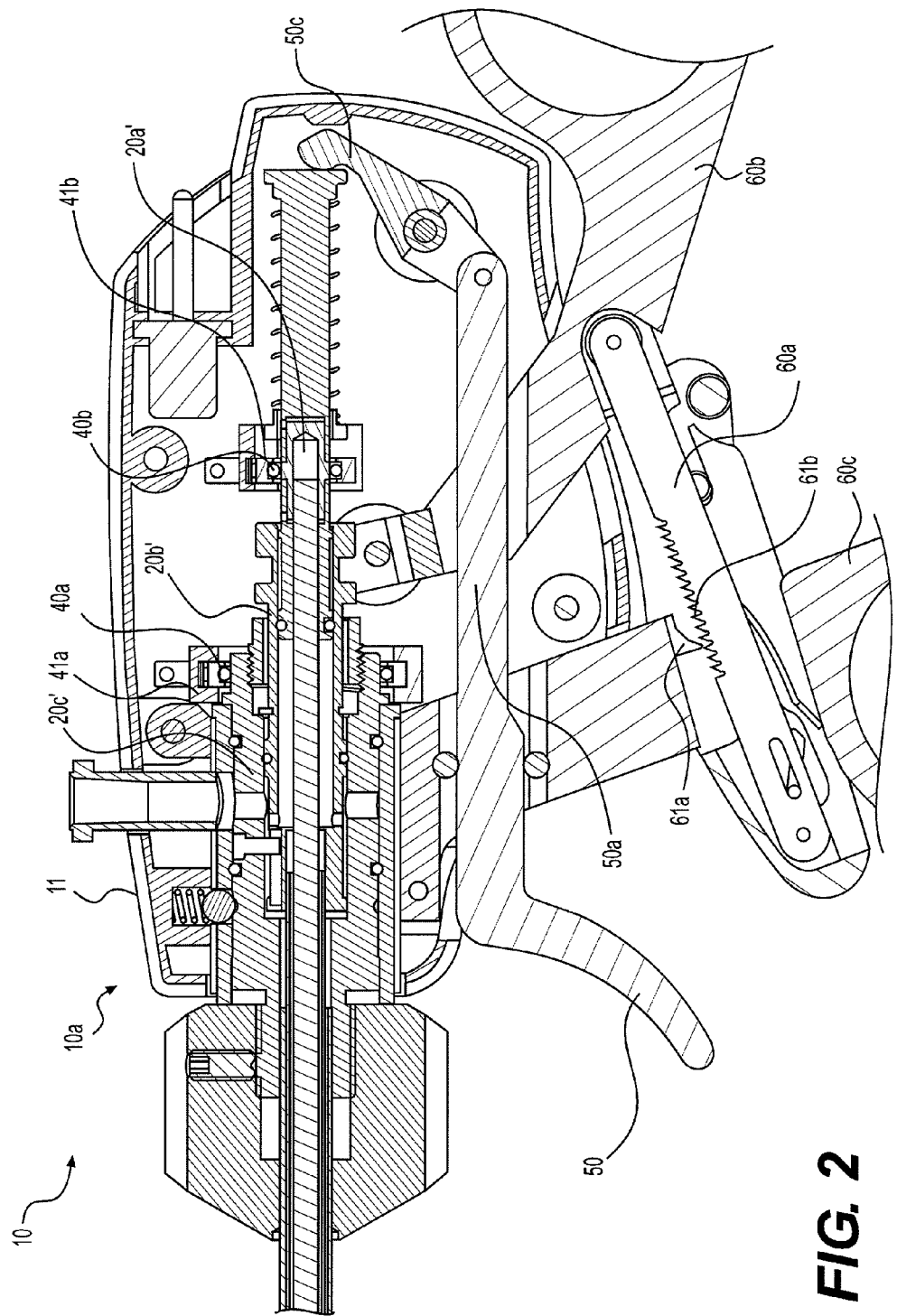
FIG. 2 is a cross-sectional view of a proximal end of the bipolar surgical instrument of FIG. 1 showing the positioning of the components of the bipolar surgical instrument when the hand-piece and jaws are opened, and the cutting-blade is retracted.

Referring to the drawings, FIG. 2 shows a cross-sectional view of a proximal end 10a of the bi-polar surgical instrument 10 according to a non-limiting embodiment of the present invention. In this regard, as illustrated in FIGS. 1 and 2, the bipolar surgical instrument may include an inner shaft assembly 20a, an intermediate shaft assembly 20b and an outer shaft assembly 20c. Additionally, the inner 20a, intermediate 20b, and outer shaft assemblies 20c, respectively, may include inner 20a', intermediate 20b', and outer shafts 20c'. Further, the inner 20a, intermediate 20b, and outer shaft assemblies 20c may be generally positioned within each other. For example, any of the shafts (e.g., any one of 20a, 20b, 20c) may protrude outwardly from any of the other shafts (e.g., any one of 20a, 20b, 20c) by a given amount. Thus, one of ordinary skill in the art would appreciate that the given amount may be anywhere from not protruding at all to several millimeters or inches, without departing from the spirit or scope of the presently claimed invention.

Additionally, a trigger 50 may be coupled to and configured to actuate the inner shaft assembly 20a; and a hand-piece 60 may be coupled to and configured to actuate the intermediate shaft assembly 20b. Further, at least one electrical contact 40 may electrically contact a peripheral surface of at least one of the inner 20a', intermediate 20b' and outer shafts 20c'. In this regard, the at least one electrical contact 40 may be configured to allow relative rotational movement and axial movement between a main body housing 11 of the surgical instrument and the at least one of the inner 20a', intermediate 20b' and outer shafts 20c' which the electrical contact 40 contacts. In the figures, the intermediate shaft assembly 20b is shown configured to move axially and rotationally with respect to the housing; however, it is readily appreciable by those skilled in the art that there may be relative rotational movement between any and all of the inner 20a', intermediate 20b and outer 20c shaft assemblies and the main body housing 11. For example, the outer shaft assembly 20c may be fixed against axial movement and configured for relative rotational movement. The intermediate 20b and inner shaft 20a assemblies may be configured for both axial movement and relative rotational movement. Additionally, the inner shaft assembly 20a may be configured to move axially while being fixed against relative rotational movement.

"Relative rotational movement" is defined herein as rotational movement of the at least one of the inner 20a', intermediate 20b' and outer shafts 20c' relative to the main body housing 11, or rotational movement of the main body housing 11 relative to the at least one of the inner 20a', intermediate 20b' and outer shafts 20c'. In other words, the main body housing 11 may rotationally move while the at least one of the inner 20a', intermediate 20b' and outer shafts 20c' is rotationally stationary; the at least one of the inner 20a', intermediate 20b' and outer shafts 20c' may rotationally move while the main body housing 11 is rotationally stationary; and the at least one of the inner 20a', intermediate 20b' and outer shafts 20c' may rotationally move while the main body housing 11 rotationally moves in an opposite rotational direction.

Further, the trigger 50 (e.g., a first connector) may not actuate the inner shaft assembly 20a depending on the type of surgical tool assembly (e.g., surgical tool assemblies 200 and 200", discussed in further detail below) which is connected to the bi-polar surgical instrument 10. For example, an elongated connector (311 and 311", discussed in further detail below) may be coupled to a distal end of the inner shaft assembly 20a and a pivot pin 260 (e.g., fixed against axial movement with respect to the outer shaft assembly 20c) of the fixed outer shaft assembly 20c, thereby preventing actuation of the inner shaft assembly 20a.

Further, one of ordinary skill in the art would readily understand that the trigger 50 may be omitted from the bi-polar surgical instrument 10 when operation of the bi-polar surgical instrument 10 does not require axial movement of the inner shaft assembly 20a, e.g., when utilizing one of the surgical tool assemblies 200 and 200", discussed in further detail below.

Figure 3:
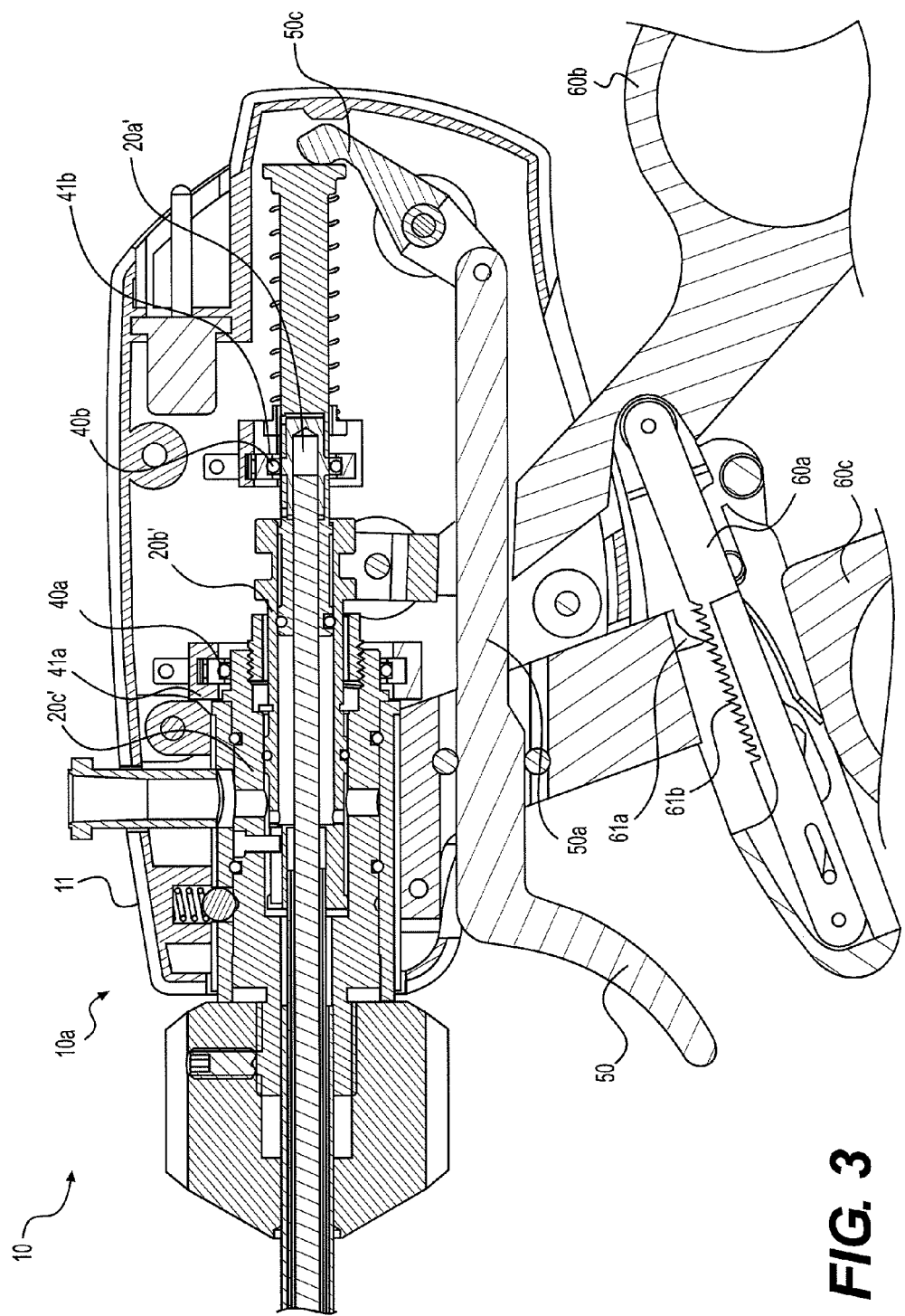
FIG. 3 is a cross-sectional view of a proximal end of the bipolar surgical instrument of FIG. 1 showing the positioning of the components of the bipolar surgical instrument when the hand-piece and jaws are closed, and the cutting-blade is retracted.
Figure 4:
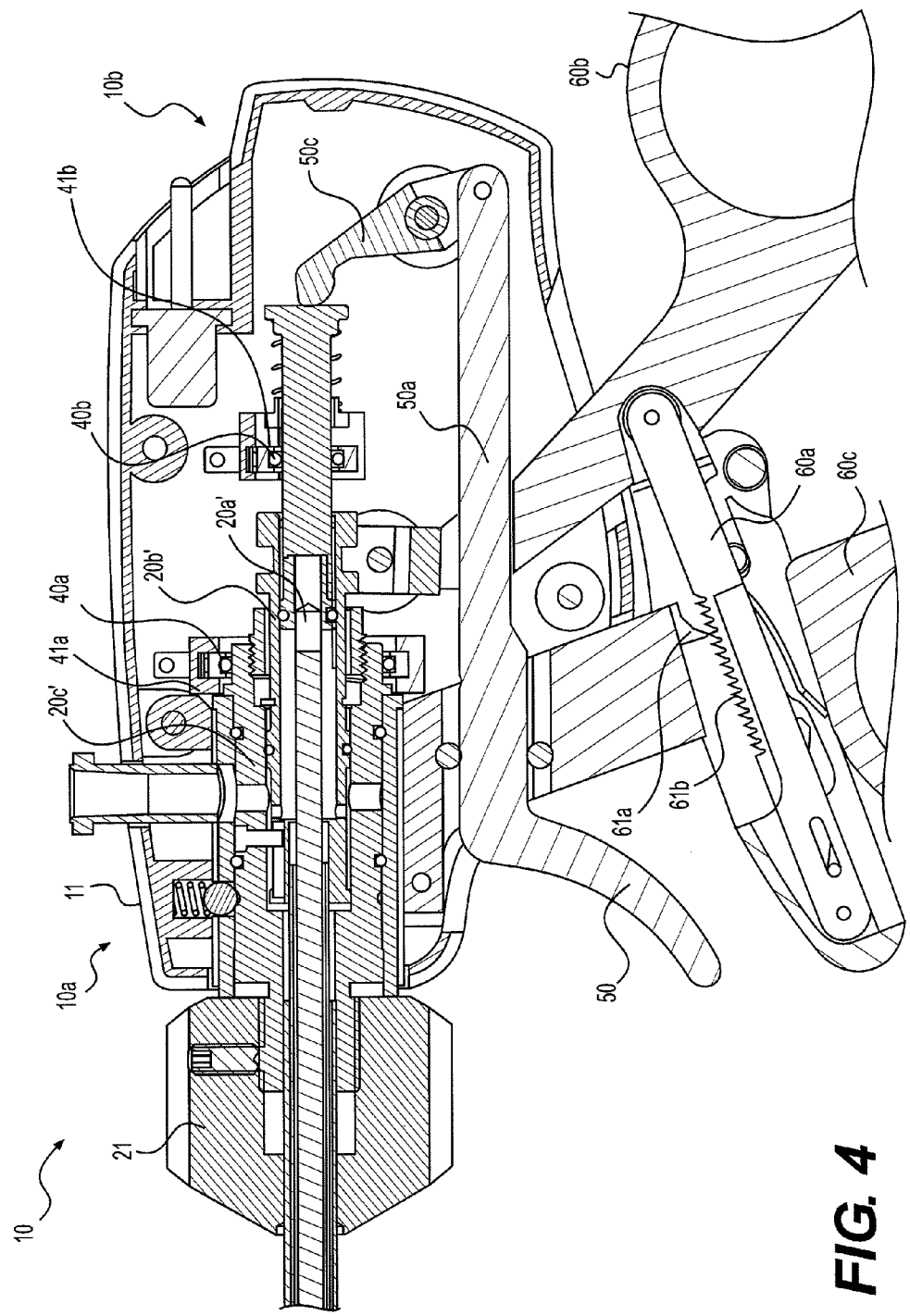
FIG. 4 is a cross-sectional view of a proximal end of the bipolar surgical instrument of FIG. 1 showing the positioning of the components of the bipolar surgical instrument when the hand-piece and jaws are closed, and the cutting-blade is extended.

Further, FIGS. 2-4 show cross-sectional views illustrating the proximal end 10a of the bipolar surgical instrument 10 in varying degrees of actuation. More specifically, FIG. 2 shows a positioning of the components of the proximal end 10a of the bipolar surgical instrument 10 when the hand-piece (e.g., a handle) 60 and trigger 50 are not depressed (e.g., when the hand-piece 60 and trigger 50 are in a fully-open position). In this regard, as shown in FIG. 2, the hand-piece 60 may include a ratchet assembly (e.g., a spring-ratchet type assembly) 60a coupling a movable thumb-piece (e.g., a handle thumb) 60b to a stationary-grip 60c, and the thumb-piece 60b may be coupled to and configured to actuate the intermediate shaft assembly 20b. Further, the trigger 50 may include an elongated shaft 50a coupled to a toggle-link 50c, e.g., the toggle-link 50c may be coupled to and configured to actuate the inner shaft assembly 20a.

Referring to FIG. 3, a positioning of the components of the proximal end 10a of the bipolar surgical instrument 10 is shown when the hand-piece 60 is depressed and the trigger 50 is in a fully-open position. In this regard, the intermediate shaft assembly 20b may be configured to move proximally, thereby actuating a first surgical tool (e.g., jaws, discussed in further detail below) which may be provided at a distal end of the bi-polar surgical instrument 10. For example, again referring to FIG. 3, an engagement tooth 61a provided on the stationary-grip 60c may move in a proximal direction to engage a plurality of opposing ratchet teeth 61b, thereby actuating the intermediate shaft assembly 20b in a proximal direction.

Referring now to FIG. 4, positioning of the components of the proximal end 10a of the bipolar surgical instrument 10 is shown when both the hand-piece 60 and the trigger 50 are depressed. In this regard, the positioning of the stationary-grip 60c may be the same as discussed in reference to FIG. 3. Further, FIG. 4 shows the positioning of the toggle-link 50c when the trigger 50 is depressed. In this regard, the toggle-link 50c may be configured to be actuated in a distal direction upon depression of the trigger 50, thereby actuating the inner shaft assembly 20a in a distal direction. In this regard, when the inner shaft assembly 20a moves in the distal direction a second surgical tool (e.g., a cutting-blade discussed in further detail below), provided at a distal end of the bi-polar surgical instrument 10, may be actuated.

However, one of ordinary skill in the art would recognize that any suitable arrangement which is configured to actuate any of the components of the shafts (i.e., including but not limited to any one of the inner, intermediate and outer shaft assemblies) may be employed without departing from the spirit in scope of the present invention. For example, opening of the hand-piece could result in the intermediate shaft assembly being actuated in a proximal direction.

Now referring to FIG. 2, the at least one electrical contact 40 may be a canted coil spring. Further, the at least one electrical contact 40 may be provided within at least one gland 41 fixedly provided within the main body housing 11.

For example, the electrical contact 40 may include a canted coil spring like those manufactured by BAL SEAL Engineering Co. Inc. to make electrical contact between at least one of the inner 20a', intermediate 20b' and outer 20c' shafts and the main body housing 11, thereby allowing for bi-directional continuous rotation (i.e., uninterrupted), as well as axial movement of the shaft which is contacted by the electrical contact 40. In other words, the shaft which is contacted by the electrical contact can be rotated indefinitely and without a limiting stop in either direction.

That is, the use of a canted coil spring may provide constant contact between at least one of the shafts and the main body housing 11 while allowing both the shaft (i.e., one of the inner 20a', intermediate 20b' and outer 20c' shafts) and the main body 11 to move rotationally (i.e., continuously and without a limit stop) and axially relative to each other. Thus, by providing constant contact between at least one of the shafts 20a', 20b' and 20c' and the electrical contact 40 power can be transferred at any time, irrespective of the rotational position of the shafts 20a', 20b' and 20c'. Additionally, when the electrical contact 40 is provided as a canted coil spring, the electrical contact 40 is tolerant of misalignment thereby eliminating positioning concerns associated with electrical contacts of the conventional art. Further, a cross-section of the surgical instrument 10 which is configured to be inserted into a patient's body can be reduced [i.e., since conducting wires provided in the shaft of the bipolar surgical instrument (to electrical connect a surgical end of the instrument to a power source) are not needed]. Thus, a non-limiting embodiment of the present invention has at least an additional advantage over the conventional art, of providing a less invasive bipolar surgical instrument 10.

Further, one of ordinary skill in the art would recognize that any suitable arrangement or structure (e.g., a compliant O-ring, etc.) which provides constant contact between at least one of the shafts and the main body housing, while allowing both the shaft and the main body to move rotationally (e.g., continuously) and axially relative to each other, may be employed without departing from the spirit and scope of the present invention According to another feature, and as illustrated in FIGS. 2-4, the at least one electrical contact 40 may include first 40a and second electrical contacts 40b. In this regard, the first electrical contact 40a may contact a surface of the outer shaft 20c' and the second electrical contact 40b may contact a surface of the inner shaft 20a'. Further, the at least one gland 41 may include first 41a and second glands 41b which receive the corresponding first 40a and second 40b electrical contacts, the first contact 40a electrically connecting the outer shaft assembly 20c to the first gland 41a and the second contact 40b electrically connecting the inner shaft assembly 20a' to the second gland 41b.

Further, as shown in FIG. 1, the outer shaft assembly 20c may provide the surgical instrument 10 with a first electrical conductor $C_1$ having a first pole; and the inner shaft assembly 20b may provide the surgical instrument 10 with a second electrical conductor $C_2$ having a second pole, the first and second poles being polar opposites.

Additionally, the first and second electrical contacts 40a, 40b may electrically couple the outer 20c' and inner shafts 20a' to each other. Further, the at least one of the inner 20a,  intermediate 20b and outer shaft 20c assemblies may be configured to rotate continuously (i.e., without a limit stop).

Additionally, either one of the shaft assemblies (e.g., 20a, 20b, and 20c) may also include a rotation knob 21 configured to rotate, e.g., the outer shaft assembly 20c. In this regard, the rotation knob 21 may be provided at a distal end of the outer shaft 20c' and rotationally coupled to the outer shaft 20c'. Further, the outer shaft 20c' may be rotationally coupled to the intermediate shaft 20b'. Further, the knob 21 may be configured to continuously rotate at least one of the inner 20a', intermediate 20b', and outer shaft assemblies 20c'.

For example, as discussed supra, when the thumb-piece 60b is depressed, the intermediate shaft assembly 20b may be actuated in a proximal direction. Further, when the trigger 50 is depressed, the inner shaft assembly 20a may be actuated in a distal direction.

Figure 5:
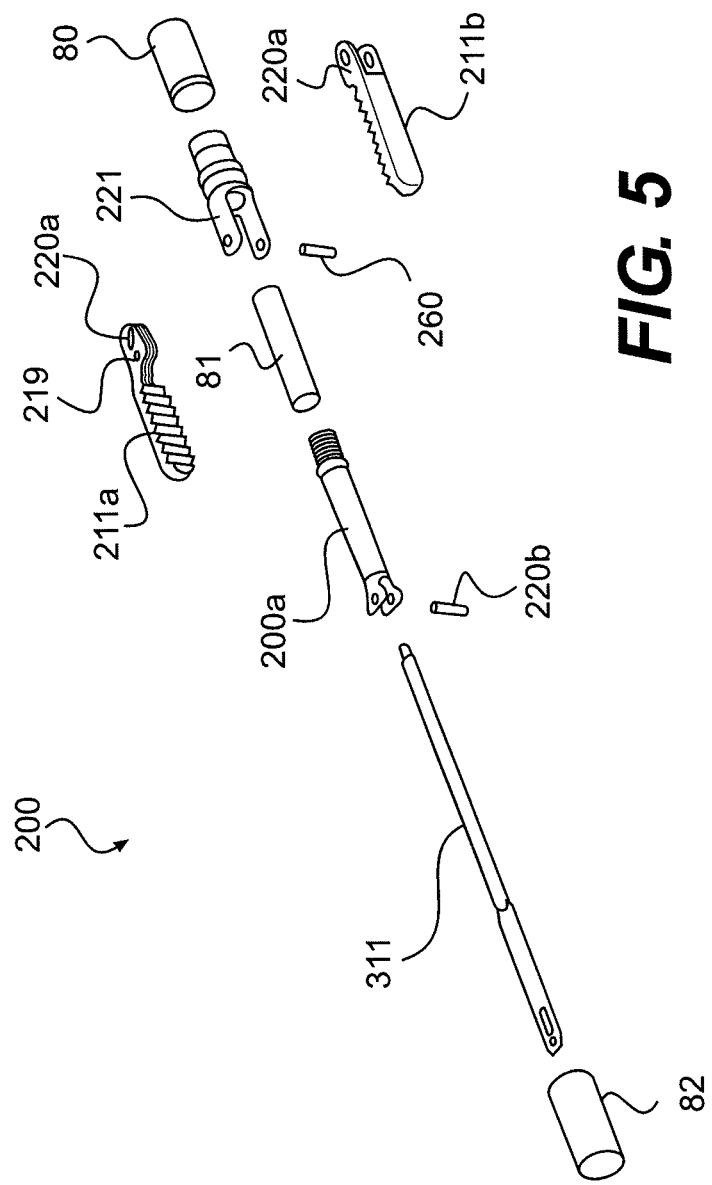
FIG. 5 is an exploded view of a surgical tool assembly according to a first non-limiting embodiment of the present invention.

Further, referring to the first non-limiting embodiment of FIG. 5, the intermediate shaft assembly may include a plunger 200a coupled to a distal end of the intermediate shaft 20b, the plunger 200a being configured to be actuated with actuation of the intermediate shaft 20b (e.g., by depressing a thumb-piece 60b). Additionally, oppositely facing jaws 211a, 211b may be coupled to a distal end of the plunger 200a and be configured to open and close via actuation of the plunger 200a. Further, the intermediate shaft assembly 20b may also include a cam 220a provided at a proximal end of each of the jaws 211a, 211b, and a cam follower 220b coupled to the distal end of the plunger 200a. In this regard, the cam follower 220b may be actuated by axial movement of the plunger 200a such that the jaws 211a, 211b open and close in accordance with a direction of axial movement of the plunger 200a.

In accordance with an additional feature, and as shown in FIG. 5, the outer shaft assembly may include a jaw support (e.g., a yoke) 221 coupled to a distal end of the outer shaft assembly 20c and a jaw pivot 219 of the jaws. In this regard, the jaws 211a, 211b may be supported at and configured to pivot about the jaw pivot 221. Additionally, the outer shaft assembly 20c may be fixed against axial movement.

Additionally, as shown in FIG. 5, the inner shaft assembly 20a may include an elongated conductor 311 coupled to the inner shaft 20a'. In this regard, the elongated conductor 311 may be configured to provide an electrical pathway for electrically connecting one of the jaws 211a, 211b to the bipolar surgical instrument 10 (e.g., by electrically connecting one of the jaws 211a, 211b to one of the first and second electrical conductors $C_1$ and $C_2$). In this regard, the inner shaft assembly 20a may be fixed against both axial movement and rotation. Additionally, the inner 20a', intermediate 20b', and outer shafts 20c' may be provided within a main body housing 11 (as shown in FIG. 3) of the surgical instrument 10.

Figure 6:
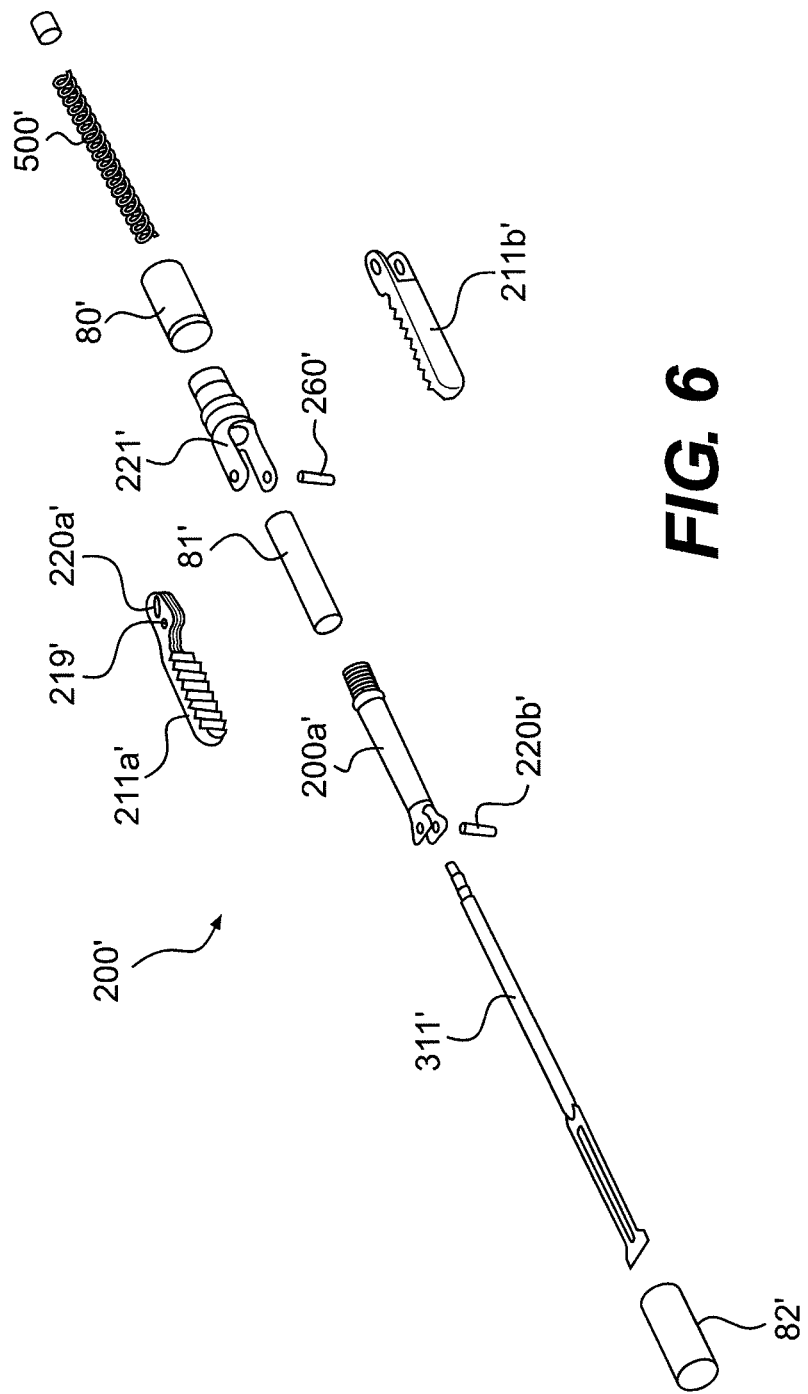
FIG. 6 is an exploded view of a surgical tool assembly according to a second non-limiting embodiment of the present invention
Figure 7:
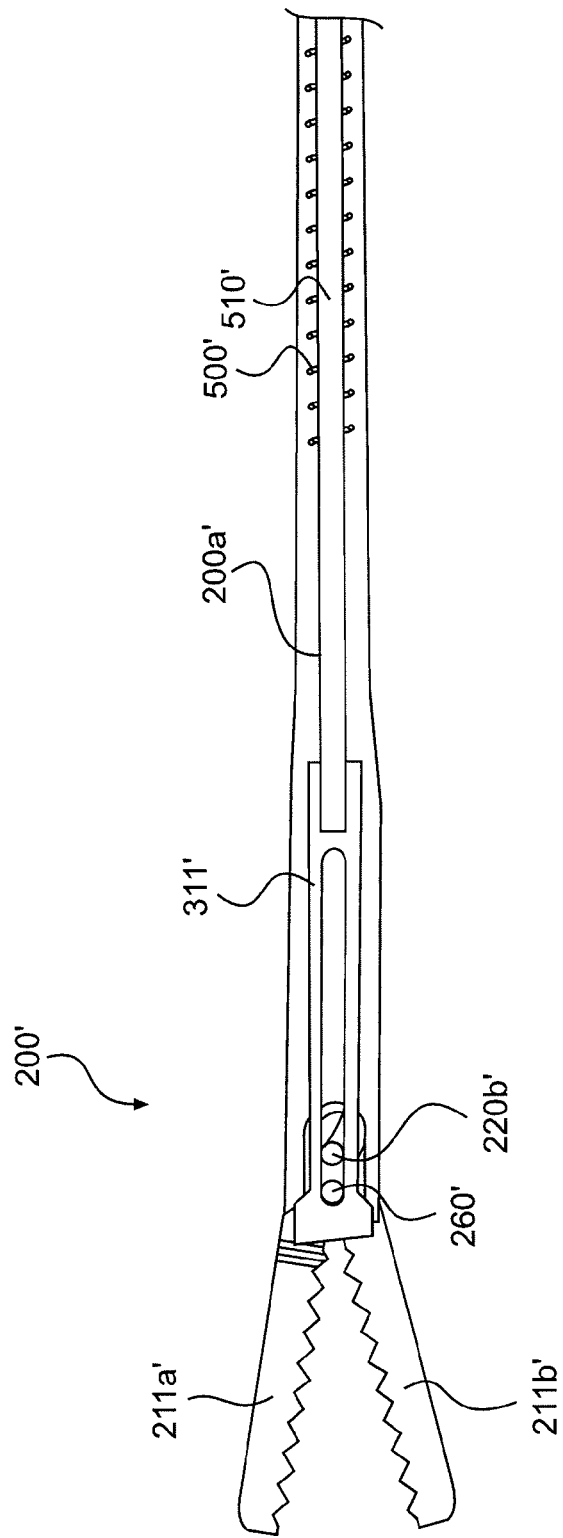
FIG. 7 is a cross-sectional view of the surgical tool assembly of FIG. 6 showing the tool assembly of the second non-limiting embodiment when the jaws are open.
Figure 8:
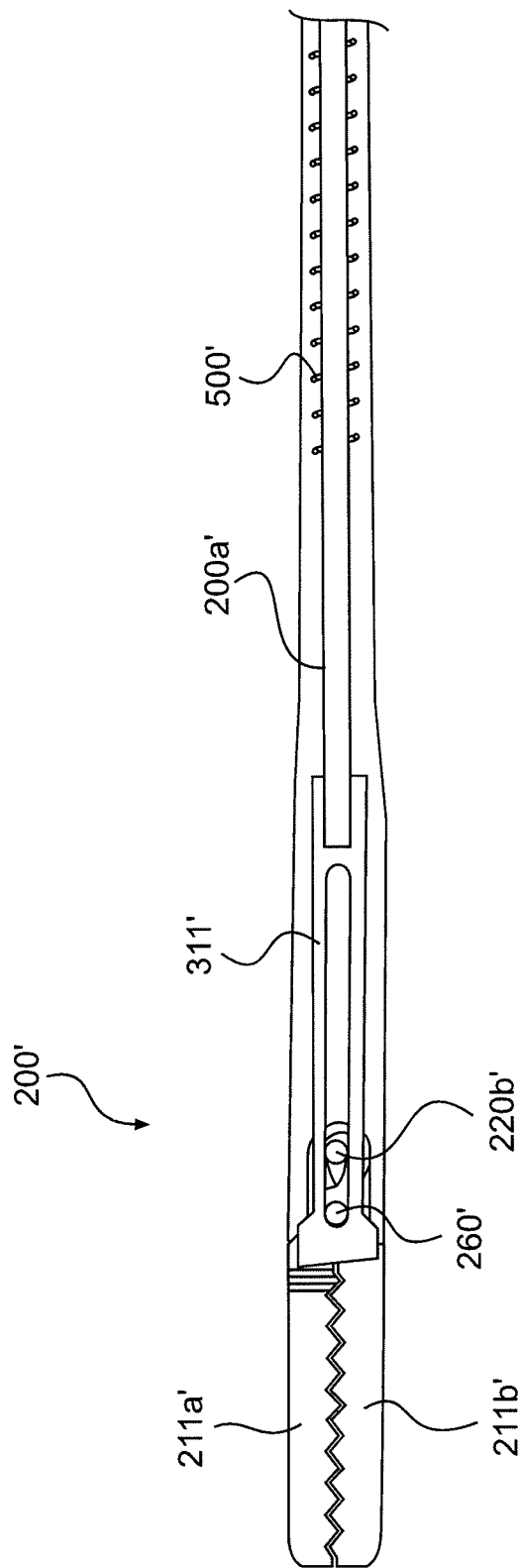
FIG. 8 is a cross-sectional view of the surgical tool assembly of FIG. 6 showing the tool assembly of the second non-limiting embodiment when the jaws are closed and having a biasing element provided at a proximal end thereof.

Further, the second non-limiting embodiment, as shown in FIG. 6, may be somewhat similar to the first non-limiting embodiment, discussed supra. In this regard, the intermediate shaft assembly may include a plunger 200a' coupled to a distal end of the intermediate shaft 20b, the plunger 200a' being configured to be actuated with actuation of the intermediate shaft 20b (e.g., by depressing a thumb-piece 60b). Additionally, oppositely facing jaws 211a', 211b' may be coupled to a distal end of the plunger 200a' and be configured to open (as shown in FIG. 7) and close (as shown in FIG. 8) via actuation of the plunger 200a'. Further, the intermediate shaft assembly 20b may also include a cam 220a' provided at a proximal end of each of the jaws 211a', 211b', and a cam follower 220b' coupled to the distal end of the plunger 200a'. In this regard, the cam follower 220b' may be actuated by axial movement of the plunger 200a' such that the jaws 211a', 211b' open and close in accordance with a direction of axial movement of the plunger 200a'.

Similar to the first non-limiting embodiment, (as shown in FIG. 6) the outer shaft assembly of the second non-limiting embodiment may include a jaw support (e.g., a yoke) 221' coupled to a distal end of the outer shaft assembly 20c and a jaw pivot 219' of the jaws. In this regard, the jaws 211a', 211b' may be supported at and configured to pivot about the jaw pivot 221'. Additionally, the outer shaft assembly 20c may be fixed against axial movement.

Further, as shown in FIG. 6, the inner shaft assembly 20a in accordance with the second non-limiting embodiment may include a blade 311' coupled to the inner shaft 20a', the blade 311' being configured to move in distal and proximal directions via actuation of the inner shaft assembly 20a. In this regard, the inner shaft assembly 20a may be fixed against rotation. Additionally, the inner 20a', intermediate 20b', and outer shafts 20c' may be provided within a main body housing 11 (as shown in FIG. 3) of the surgical instrument 10. In this regard, the cutting blade 311' may be configured to bisect tissue which may be grasped by the opposing jaws 211a', 211b'.

Discussing the bi-polar surgical instrument in further detail, the first 40a and second 40b electrical contacts may electrically contact corresponding peripheral surfaces of the inner 20a' and outer shafts 20c'. In this regard, the first 40a and second 40b electrical contacts may be configured to allow relative rotational movement and axial movement between the first 40a and second 40b electrical contacts and the corresponding inner 20a' and outer shafts 20c' which the first 40a and second 40b electrical contacts contact.

Further, the outer shaft assembly 20c may provide the surgical instrument 10 with a first electrical conductor $C_1$ having a first pole electrically connected to a first gland 41a which receives the first electrical contact 40a and the inner shaft assembly 20a may provide the surgical instrument 10 with a second electrical conductor $C_2$ having a second pole electrically connected to a second gland 41b which receives the second electrical contact 40b. In this regard, the first and second poles may be polar opposites.

In addition to the bipolar surgical instrument discussed supra, the present invention may provide a surgical tool assembly 200 (as well as 200' or 200", discussed in further detail below) configured to be connected (e.g., detachably connected) to a distal end of a bipolar surgical instrument 10. The surgical tool assembly 200, as illustrated in FIG. 5, may include oppositely facing first and second jaws 211a, 211b (as well as 211a', 211b' or 211a", 211b") which are configured to open and close. Further, tubes 80 and 82 (as well as 80' and 82' or 80" and 82") may be provided in order to couple components provided at a distal end of the surgical tool assembly 200. For example, tubing 80 may be configured to couple the support (e.g., a yoke) 211 to the outer shaft assembly 20c', and tubing 82 to may provide insulation for a tip of the surgical tool assembly 200. Additionally, tubing 81 (as well as 81' or 81") may insulate (e.g., electrically insulate) the intermediate shaft assembly 20b' from the outer shaft assembly 20c' at a distal end of the surgical tool assembly 200.

More particularly, the surgical tool assembly 200 may include a composite pivot pin 260 (as well as 260') which includes a conductive material A and a non-conductive (insulator) material B, the pivot pin 260 pivotally coupling the first 211a and second jaws 211b. Further, the first jaw 211a may be electrically connected to a first conductive region $R_1$ of the composite pivot pin 260 and the second jaw 211b may be electrically connected to a second conductive region $R_2$ of the composite pivot pin 260. Additionally, the non-conductive material B may electrically isolate the first $R_1$ and second $R_1$ conductive regions of the conductive material A from each other. In this regard, it should be appreciated that the composite pivot pin 260 has at least one advantage of being a much less costly and complicated construction than a composite jaw or blade construction. Additionally, one of ordinary skill in the art would recognize that the number of conductive regions may vary.

Further, as shown in FIG. 8, the conductive material A may have a metal provided on a surface of the conductive material A; and the non-conductive material B may have a ceramic material provided on the surface of the non-conductive material B. For example, the pivot pin 260 may include a ceramic material, which provides the non-conductive material B of the composite pivot pin 260, and the ceramic material A may be provided with a metal coating which provides the conductive material of the composite pivot pin 260; or the pivot pin 260 may include a metal material, which provides the conductive material of the composite pivot pin 260, and the metal material may be provided with a ceramic coating which provides the non-conductive material B of the composite pivot pin 260.

For example, still referring to FIG. 8, the first and second conductive coatings may be provided on a surface of the composite pivot pin 260. Additionally, the first and second conductive coatings may be spaced from each other along an axis of rotation of the composite pivot pin 260. In this regard, the first conductive region may be configured to electrically connect the first jaw 211a to the first electrical conductor $C_1$ and the second conductive region may be configured to electrically connect the second jaw to the second electrical conductor $C_2$. Thus, the first jaw 211a may be configured to provide a first electrode having a first pole and the second jaw 211b may be configured to provide a second electrode having a second pole, the first and second poles being polar opposites.

Referring to FIGS. 6-8, a cutting-blade 311' configured to retractably extend between the first 211a' and second 211b' jaws may be provided. In this regard, the cutting-blade 311' may be configured to engage the second conductive region of the pivot pin 260' (or 260) to electrically connect the second jaw 211b' to the second conductor $C_2$.

Further, as illustrated in FIG. 6, the composite pivot pin 260' may extend through a slot S provided in the cutting-blade 311', and the second conductive region may be provided on a surface of the composite pivot pin 260' which contacts an inner surface of the slot S to provide the electrical connection between the second jaw 211b' and the second conductor $C_2$.

Additionally, referring to FIG. 5 again, a cam 220a (as well as 220a' or 220a") may be provided at a proximal end of the first 211a and second 211b jaws and a cam follower 220b (as well as 220b' or 220b") may be coupled to the cam 220a and a distal end of a plunger 200a (as well as 200a' or 200a") which is configured to reciprocate axially. Thus, when the plunger 200a moves axially the cam follower 220b may be actuated such that the first 211a and second 211b jaws open and close in accordance with a direction of axial movement of the plunger 200a. Further, the plunger 200a may include a non-conductive material, the plunger 200a being configured to be electrically isolated from the first $C_1$ and second $C_2$ conductors. Also, pivot holes 219 (as well as 219' or 219") may be provided in proximal ends of the first 211a and second 211b jaws, the pivot holes 219 may be configured to receive the composite pivot pin 260 (or insulating pin 260").

Further, the surgical tool assembly of FIG. 5 may include a jaw support 211 (as well as 211a' and 211') which is configured to pivotally receive the composite pivot pin 260 such that the first 211a and second 211b jaws are coupled to and configured to pivot about the jaw support 211. Further, as shown in FIG. 6, a spring 500' may be coupled to a proximal end of the plunger 200a' and a cutting-blade support 510' provided on a proximal end of the cutting-blade 311'. In this regard, the spring 500' may be configured to bias the cutting-blade 311' in a proximal direction such that increased engagement between the cutting-blade 311' and the second conductive region of the composite pivot pin 260' is provided.

Figure 9:
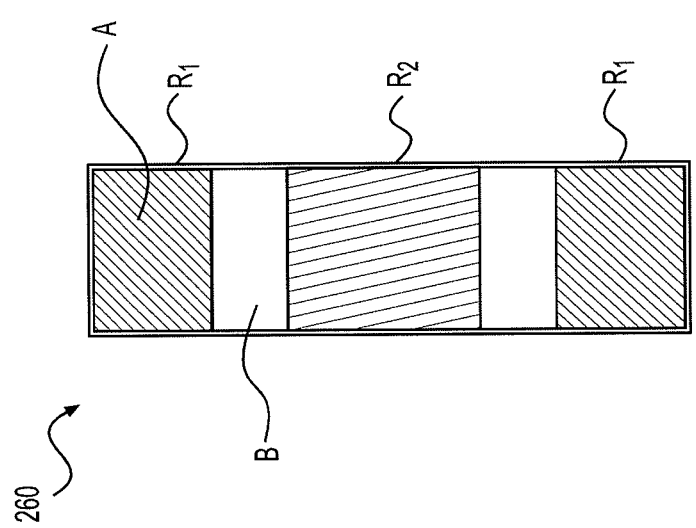
FIG. 9 is a plan view of a non-limiting embodiment of a pivot pin.

When the surgical tool assembly 200' and the bi-polar surgical instrument 10 are assembled, as shown in FIG. 9, the second connector (e.g., thumb-piece 60b) of the bi-polar surgical instrument 10 may be coupled to and configured to actuate first 211a' and second 211b' jaws of the surgical tool assembly 200'. Further, a first connector (e.g., trigger 50) of the bipolar surgical instrument 10 may be coupled to and configured to actuate the cutting-blade 311' of the surgical tool assembly 200'.

In other words, the first connector (e.g., trigger 50) may be coupled to and configured to actuate the inner shaft assembly 20a which may have a cutting-blade 311' connected to a distal end thereof. Further, the second connector (e.g., thumb-piece 60b) may be coupled to and configured to actuate the intermediate shaft assembly 20b. Additionally, the first 211a' and second 211b' jaws may be connected to a distal end of the intermediate shaft assembly 20b and pivotally connected to a distal end of the outer shaft assembly 20c.

Figure 10:
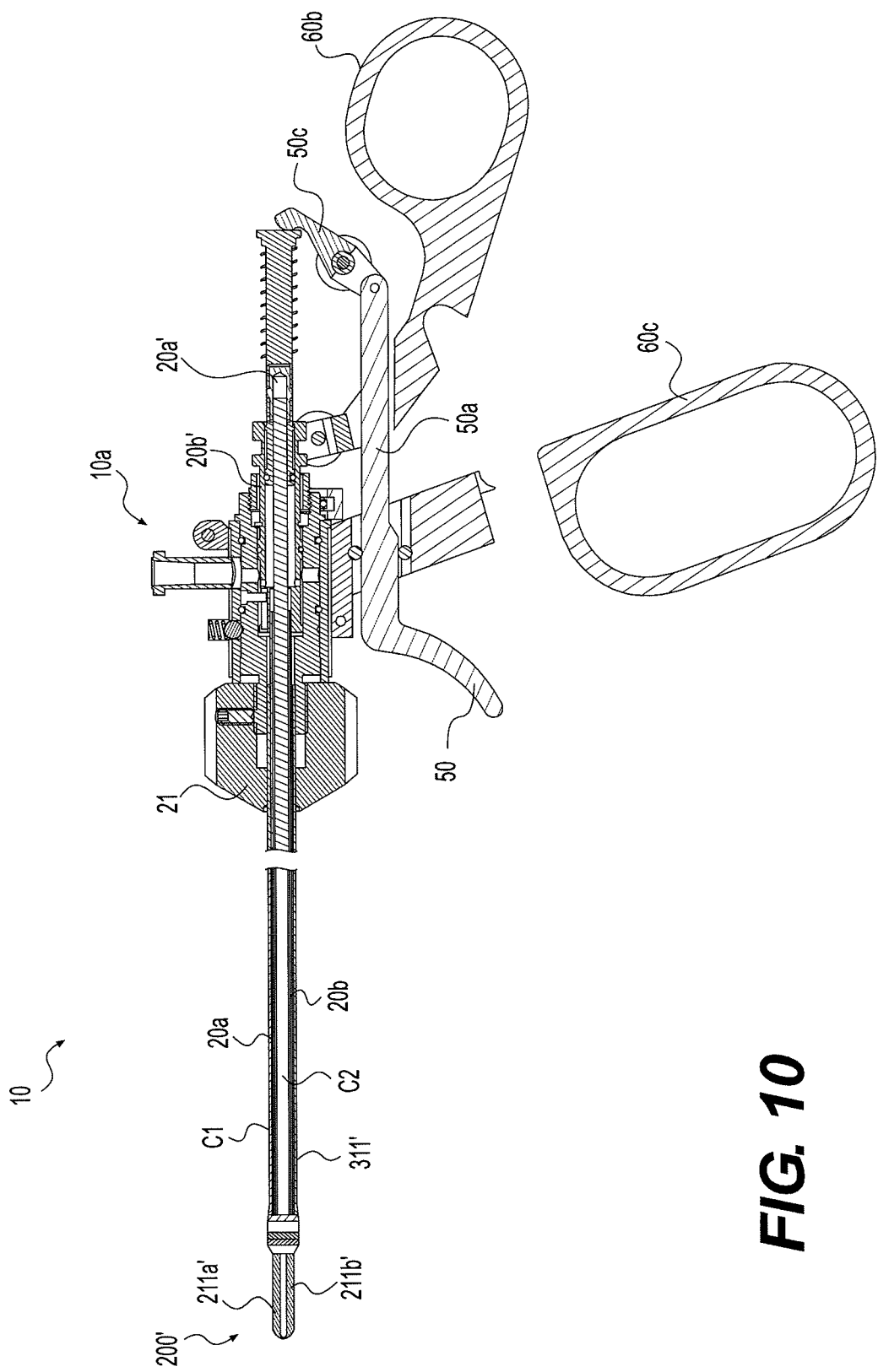
FIG. 10 shows a cross-sectional view of the surgical tool assembly of FIG. 6 coupled to the bipolar surgical instrument of FIG. 1.

Although, FIG. 10 is shown having the surgical tool assembly 200' which includes a cutting blade 311' attached thereto, one of ordinary skill in the art would readily appreciate that the surgical tool assembly 200 (which includes the elongated electrical connector 311 and 311") may also be connected to the bipolar surgical instrument 10. Further, the surgical tool assembly 200", discussed in further detail below, may also be connected to the bipolar instrument 10 in a manner similar to surgical tool assemblies 200 and 200'. In this regard, as discussed supra, the first connector and the inner shaft assembly 20a may be fixed against axial and relative rotational movement when either one of the surgical tool assemblies 200 or 200" are connected to the bipolar instrument 10. That is, since the elongated electrical connectors 311 and 311" of the surgical tool subassemblies may be used as a fixed electrical pathway to electrically connect the surgical tool assembly to the bi-polar surgical instrument 10.

Now referring to FIGS. 11A-11C, the surgical tool assembly 200" may include bipolar scissors (as shown in FIGS. 11A-11C) for cutting, cauterizing and/or coagulating tissue. In this regard, the scissor 211" may include a first blade 211a" having a first cutting edge 252a and a first shearing blade surface 253a and a second blade 211b" having a second cutting edge 252b and a second shearing blade surface 253b. Further, one of the first 211a" and second 211b" blades may include a non-conductive material having an embedded electrode 700a or 700b, while the other of the blades may be of a conventional conductive or non-conductive material. Also, only one of the blades may be provided with a metal shearing surface. In this regard, one of ordinary skill in the art would readily appreciate that numerous combinations of blades can be used without departing from the spirit and scope of the present invention.

Further, each of the first and second blades 211a", 211b" may include a non-conductive material, the first blade 211a" having a first embedded electrode 700a and the second blade 211b" having a second embedded electrode 700b. In this regard, the first and second electrodes 700a, 700b may be polar opposites of each other.

Additionally, as shown in FIGS. 12B and 12C, the first electrode 700a may be embedded at an outer surface of the first blade 211a" and the second electrode 700b may be embedded at an outer surface of the second blade 211b". Also, the one of the first and second blades 211a", 211b" having the embedded electrode 700a or 700b may have a metal shearing surface 710a or 710b embedded in the non-conductive material at the corresponding shearing blade surface.

Further, when both the first and second blades 211a", 211b" include a non-conductive material, a first metal shearing surface $M_1$ may be embedded in the non-conductive material at the first shearing blade surface of the first blade 211a" and the second blade 211b" may include a second metal shearing surface $M_2$ embedded in the non-conductive material at the second shearing blade surface. Further, the non-conductive material may electrically isolate the embedded electrode from the corresponding metal shearing blade surface. Also, only one metal surface $M_1$, $M_2$ may be used. Further, the metal surfaces may be made of any suitable metal, as well as any suitable combination of metals. Additionally, the metal surfaces $M_1$ and $M_2$ may be provided with additional insulation, e.g. a non-conductive coating, to prevent electrical interference between the electrodes 700a and 700b and the metal surfaces $M_1$ and $M_2$.

Figure 12D:
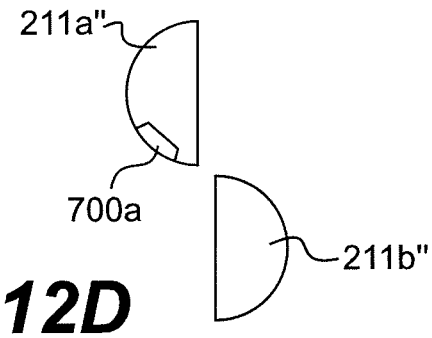
FIG. 12D is a cross-sectional view of the scissor having, e.g., a ceramic blade having a metal insert and a metal blade.

Additionally, the non-conductive material, of the at least one of the first 211a" and second 211b" blades, may include a ceramic material and the embedded electrode 700a may include a metal insert, as shown in FIG. 12D. Further, the other of the at least one of the first 211a" and second 211b" blades may include metal.

Figure 12E:
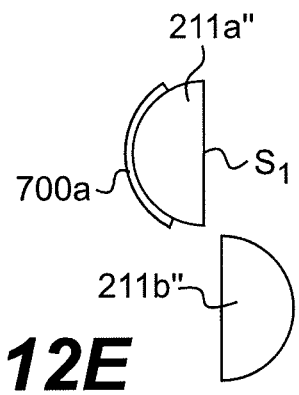
FIG. 12E is a cross-sectional view of the scissor having, e.g., a ceramic blade having a metal coating and a metal blade.

Further, as shown in FIG. 12E, at least one of the first 211a" and second 211b" blades may include a non-conductive material having an electrode 700a. In this regard, the electrode 700a may be provided as a metal coating opposite the shearing blade surface S1 of the at least one of the first 211a" and second 211b" blades which includes the non-conductive material. Additionally, the non-conductive material may include a ceramic material and the other of the at least one of the first 211a" and second 211b" blades may include metal.

Figure 12F:
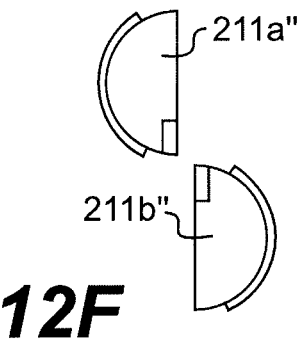
FIG. 12F is a cross-sectional view of the scissor having, e.g., two ceramic blades, each having a metal coating.

Further, as shown in FIG. 12F, both the first 211a" and second 211b" blades may include a non-conductive material. In this regard, each of the first and second blades may have a metal insert provided at corresponding cutting edges of the first and second blades. Further, the metal coating may be provided on both the first and second blades opposite corresponding shearing blade surfaces. Further, the non-conductive material may include a ceramic material.

Further, the non-conductive material may include a ceramic material. However, one of ordinary skill in the art would readily understand that any suitable non-conductive material having desirable electrical and/or mechanical properties may be employed.

Additionally, the surgical tool assembly 200a" may be configured to be connected to a distal end of a bipolar surgical instrument 10 having first and second electrical conductors $C_1$ and $C_2$. More particularly, the electrode 700a or 700b embedded in one of the first and second blades 211a", 211b" may be configured to be electrically connected to one of the first and second electrical conductors $C_1$ and $C_2$ of the bipolar surgical instrument 10.

Further, as shown in FIGS. 11B and 11C the surgical tool assembly 200" may also include an elongated electrical connector 311" (e.g., a rod or blade) which is configured to electrically connect the embedded electrode 700a or 700b of the one of the first and second blades 211a", 211b" to one of the first and second electrical conductors $C_1$ and $C_2$ of the bi-polar instrument 10.

For example, the elongated connector 311" may include a rod which is configured to electrically connect the first embedded electrode 700a to the first electrical conductor C₁. Further, the surgical tool assembly 200" may also include a blade support 221" which is configured to electrically connect the second embedded electrode 700b to the second electrical conductor C₂. However, one of ordinary skill in the art would readily understand that any suitable element capable of electrically connecting the surgical tool assembly 200" to the bipolar surgical instrument 10 may be provided.

Referring to 11B, the elongated connector 311" (e.g., a rod) may include a spring 311$_S$" provided at a distal end of the elongated connector 311". In this regard, the spring 311$_S$" may be configured to bias the first blade 211a" into contact with the second blade 211b" and electrically connect the first blade 211a" to one of the first and second electrical conductors C₁ and C₂. Additionally, the blade support 221" may include a generally fork-shaped (i.e., pronged) shaft 221" provided at a distal end of the surgical tool assembly 200". In this regard, the spring 311$_S$" may be resiliently pressed an interior of the blade support 221" so that the first and second blades 211a", 211b" are forced into contact.

Additionally, the surgical tool assembly 200" may also be provided with a cam arrangement similar to the preceding surgical tool assemblies 200' and 200". Further, as discussed above, the surgical tool assembly 200" may be connected to the bipolar surgical instrument 10 in a manner similar to surgical tool assemblies 200 and 200".

Further, as shown in FIG. 12C and FIG. 13, the second electrode 700b may be embedded in the non-conductive material of the second blade 211b", e.g., by embedding the second electrode 700b in an insert recess R2. Further, an electrical pathway may be provided by metallizing a surface of a metallization recess R1 (i.e., which receives the metallization) which is proximate the blade support 221". Further, the metallization MT which may be provided within the metallization recess R1 may be provided so as to extend into the insert recess R2 (i.e., which receives the electrode). Thus, e.g., when the second electrode 700b is brazed onto the second blade 211b", within the insert recess R2, the metallization provides a reliable electrical connection between the second electrode 700b and the blade support 221".

Further, the spring 311$_S$" may be configured to contact the metallized area of the first blade 211a" so as to provide a reliable electrical connection between the first electrode 700a and the elongated electrical conductor 311". Additionally, the larger cross-sectional area provided by the embedded electrode 700a or 700b of the present invention provides the blades 211a", 211b" with better current-carrying capabilities compared to conventional metal coatings. Further, by providing the embedded electrode 700a, 700b of the present invention, the structural integrity of the blades 211a", 211b" is not comprised due to possible weakening of the non-conductive material (e.g., a ceramic).

It is further noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A bipolar scissor for cutting and coagulating tissue, the bipolar scissor comprising:
a first blade having a first cutting edge and a first shearing blade surface;
a second blade having a second cutting edge and a second shearing blade surface;
a blade support that supports the first blade and the second blade, and
wherein at least one of the first and second blades comprises a non-conductive material having an embedded electrode,
the non-conductive material further comprising an insert recess which receives the embedded electrode and a metallization recess arranged outside of the insert recess and provided with a metallization that provides an electrical connection between the embedded electrode and the blade support, the metallization extending into the insert recess and electrically contacting the embedded electrode.

2. The bipolar scissor of claim 1, wherein the insert recess and the metallization recess are integrally formed with each other.

3. The bipolar scissor of claim 1, wherein the embedded electrode is brazed onto the non-conductive material.

4. The bipolar scissor of claim 1, wherein each of the first and second blades comprises the non-conductive material, the embedded electrode including first and second embedded electrodes, and the first blade having the first embedded electrode and the second blade having the second embedded electrode, the first and second electrodes being polar opposites of each other.

5. The bipolar scissor of claim 4, wherein the first electrode is embedded at an outer surface of the first blade and the second electrode is embedded at an outer surface of the second blade.

6. The bipolar scissor of claim 4, wherein the first blade further comprises a first metal shearing surface embedded in the non-conductive material at the first shearing blade surface and the second blade further comprises a second metal shearing surface embedded in the non-conductive material at the second shearing blade surface.

7. The bipolar scissor of claim 6, wherein the non-conductive material of the first blade electrically isolates the first embedded electrode from the first metal shearing surface and the non-conductive material of the second blade electrically isolates the second embedded electrode from the second metal shearing surface.

8. The bipolar scissor of claim 1, wherein the one of the first and second blades having the embedded electrode further comprises a metal shearing surface embedded in the non-conductive material at the shearing blade surface of the one of the first and second blades having the embedded electrode.

9. The bipolar scissor of claim 8, wherein the non-conductive material electrically isolates the embedded electrode from the metal shearing blade surface.

10. The bipolar scissor of claim 1, wherein the non-conductive material comprises a ceramic material.

11. The bipolar scissor of claim 1, wherein the other of the first and comprises a metal construction to provide the electrode.

12. The bipolar scissors according to claim 1, wherein the non-conductive material, of the at least one of the first and second blades, comprises a ceramic material and the embedded electrode comprises a metal insert, and the other of the at least one of the first and second blades comprising metal.

13. The bipolar scissor of claim 1, wherein the metallization is positioned within the metallization recess so as to be flush with an outer surface of the at least one of the first and second blades.

14. The bipolar scissor of claim 13, wherein sides of the metallization converge at a front end of the metallization.

15. A surgical tool assembly configured to be connected to a distal end of a bipolar surgical instrument having first and second electrical conductors, the surgical tool assembly comprising:
   a bipolar scissor comprising:
      a first blade having a first cutting edge and a first shearing blade surface; and
      a second blade having a second cutting edge and a second shearing blade surface, and
      at least one electrode embedded in one of the first and second blades,
   wherein the one of the first and second blades having the embedded electrode comprises a non-conductive material, the electrode being configured to be electrically connected to one of the first and second electrical conductors; and
   the surgical tool assembly further comprising:
   an elongated connector configured to electrically connect the at least one embedded electrode of the one of the first and second blades to one of the first and second electrical conductors,
   wherein the elongated connector further comprises a spring provided at a distal end of a rod, the spring being configured to bias the first blade into contact with the second blade and electrically connect the first blade to one of the first and second electrical conductors.

16. The surgical tool assembly of claim 15, wherein each of the first and second blades comprises the non-conductive material, and the embedded electrode comprising first and second embedded electrodes, and the first blade having a first embedded electrode and the second blade having a second embedded electrode, the first and second electrodes being polar opposites of each other.

17. The surgical tool assembly of claim 16, further comprising:
   the elongated connector configured to electrically connect the first embedded electrode to the first electrical conductor; and
   a blade support configured to electrically connect the second embedded electrode to the second electrical conductor.

18. The surgical tool assembly of claim 17, wherein the blade support comprises a fork-shaped shaft provided at a distal end of the surgical tool assembly.

19. The surgical tool assembly of claim 15, further comprising a blade support having a pivot pin, the first and second blades being configured to rotate about the pivot pin so as to open and close.

20. The surgical tool assembly of claim 15, further comprising:
   a first cam provided at a proximal end of the first blade;
   a second cam provided at a proximal end of the second blade; and
   a cam follower coupled to the first and second cams and a distal end of a plunger which is configured to reciprocate axially, wherein axial movement of the plunger actuates the cam follower such that the first and second blades open and close in accordance with a direction of axial movement of the plunger.

21. The surgical tool assembly of claim 15, wherein a longitudinal axis of a portion of the spring which contacts one of the first blade and the second blade is offset in a radial direction from a longitudinal axis of the rod.

22. A bipolar surgical instrument including a surgical tool assembly configured to be connected to a distal end of the bipolar surgical instrument having first and second electrical conductors, the surgical tool assembly comprising:
   a bipolar scissor including:
      a first blade having a first cutting edge and a first shearing blade surface; and
      a second blade having a second cutting edge and a second shearing blade surface, and
      at least one electrode embedded in one of the first and second blades,
   wherein the one of the first and second blades having the embedded electrode comprises a non-conductive material, the electrode being configured to be electrically connected to one of the first and second electrical conductors,
   and the bipolar surgical instrument further comprising:
   an inner shaft assembly having an inner shaft;
   an intermediate shaft assembly having an intermediate shaft;
   an outer shaft assembly having an outer shaft, the intermediate and inner shaft assemblies generally being positioned within the outer shaft assembly, and the inner shaft assembly generally being positioned within the intermediate shaft assembly;
   a first connector coupled to the inner shaft assembly;
   a second connector coupled to and configured to move the intermediate shaft assembly;
   a main body housing coupled to the first and second connectors; and
   at least one electrical contact electrically contacting a peripheral surface of at least one of the inner, intermediate and outer shafts, wherein the at least one electrical contact is configured to allow uninterrupted and continuous rotation of the main body housing relative to the at least one of the inner, intermediate and outer shafts which the electrical contact contacts.

23. The bipolar surgical instrument of claim 22, wherein the at least one electrical contact comprises a canted coil spring.

24. A bipolar scissor for cutting and coagulating tissue, the bipolar scissor comprising:
   a first blade having a first cutting edge and a first shearing blade surface;
   a second blade having a second cutting edge and a second shearing blade surface;
   a blade support that supports the first blade and the second blade, and
   at least one of the first and second blades comprising a non-conductive material having an electrode, and the electrode comprising a metal coating provided opposite the shearing blade surface of the at least one of the first and second blades comprising the non-conductive material,
   the first and second blades both comprising a non-conductive material, each of the first and second blades having a metal insert provided at corresponding cutting edges of the first and second blades, and the metal coating provided on both the first and second blades opposite corresponding shearing blade surfaces,
   the non-conductive material further comprising an insert recess which receives the embedded electrode and a metallization recess arranged outside of the insert recess and provided with a metallization that provides an electrical connection between the embedded electrode and the blade support, the metallization extending into the insert recess and electrically contacting the embedded electrode.

25. The bipolar scissors according to claim 24, the non-conductive material comprising a ceramic material, and the other of the at least one of the first and second blades comprising metal.

26. The bipolar scissors according to claim 24, the non-conductive material comprises a ceramic material.

* * * * *